United States Patent [19]

Kira

[11] Patent Number: 4,834,746
[45] Date of Patent: * May 30, 1989

[54] ARTIFICIAL VESSEL AND PROCESS FOR PREPARING THE SAME

[75] Inventor: Kazuaki Kira, Kobe, Japan

[73] Assignee: Kanegafuchi Kagaku Kogyo Kabushiki Kaisha, Osaka, Japan

[ * ] Notice: The portion of the term of this patent subsequent to Feb. 16, 2005 has been disclaimed.

[21] Appl. No.: 840,170

[22] Filed: Mar. 17, 1986

Related U.S. Application Data

[63] Continuation-in-part of Ser. No. 617,403, Jun. 5, 1984, abandoned.

[30] Foreign Application Priority Data

Jun. 6, 1983 [JP] Japan ................................. 58-101520
Mar. 1, 1984 [JP] Japan ................................. 59-39972
Mar. 7, 1984 [JP] Japan ................................. 59-44398

[51] Int. Cl.$^4$ .............................................. A61F 2/06
[52] U.S. Cl. .................................... 623/1; 623/12; 600/36
[58] Field of Search .................... 623/1, 12, 66; 128/334 R; 600/36

[56] References Cited

U.S. PATENT DOCUMENTS

| | | |
|---|---|---|
| 3,425,418 | 2/1969 | Chuapil et al. ........................... 623/1 |
| 3,745,203 | 7/1973 | Harper . |
| 3,991,147 | 11/1976 | Knipp et al. . |
| 4,173,689 | 11/1979 | Lyman et al. ....................... 623/1 X |
| 4,208,745 | 6/1980 | Okita . |
| 4,234,535 | 11/1980 | Okita . |
| 4,254,180 | 3/1981 | Kline . |
| 4,286,341 | 9/1981 | Greer et al. . |
| 4,304,010 | 12/1981 | Mano ..................................... 623/1 |
| 4,321,711 | 3/1982 | Mano . |
| 4,355,426 | 10/1982 | MacGregor ........................... 623/1 |
| 4,550,447 | 11/1985 | Seiler, Jr. et al. . |
| 4,604,762 | 8/1986 | Robinson . |
| 4,655,771 | 4/1987 | Wallsten . |
| 4,725,273 | 2/1988 | Kira ..................................... 623/1 |

FOREIGN PATENT DOCUMENTS

| | | |
|---|---|---|
| 2931 | 7/1979 | European Pat. Off. . |
| 0117072 | 8/1984 | European Pat. Off. . |
| 0130401 | 1/1985 | European Pat. Off. . |
| 2941279 | 4/1980 | Fed. Rep. of Germany . |
| 3204719 | 9/1982 | Fed. Rep. of Germany . |
| 1265246 | 3/1972 | United Kingdom . |
| 2033233 | 5/1980 | United Kingdom . |
| 2077107 | 12/1981 | United Kingdom . |
| 2092894 | 8/1982 | United Kingdom . |

OTHER PUBLICATIONS

Szycher et al, Synthetic Biomedical Polymers, Concepts and Applications, 1980, pp. 29–38.

Primary Examiner—Richard J. Apley
Assistant Examiner—Alan W. Cannon
Attorney, Agent, or Firm—Armstrong, Nikaido Marmelstein Kubovcik & Murray

[57] ABSTRACT

An artificial vessel made of an elastomer having a network structure over the entire thickness of the vessel wall with small pores having a maximum diameter of from 1 to 100 μm which communicate between the inner surface and the outer surface, and having a porosity of 75 to 87.5% by volume and a compliance of 0.1 to 0.8.

3 Claims, 1 Drawing Sheet

ARTIFICIAL VESSEL AND PROCESS FOR PREPARING THE SAME

CROSS-REFERENCE TO RELATED APPLICATION

This is a continuation-in-part of application of Ser. No. 617,403 filed on June 5, 1984, now abandoned.

BACKGROUND OF THE INVENTION

The present invention relates to an artificial vessel which has a porosity and a compliance approximate to that of a vital vessel and the process for preparation of the same.

In recent days, investigation as to an artificial vessel has proceeded and many artificial vessels have been developed with the progress of vascular surgery. At present, examples of the clinically used artificial vessels for arteries with large diameter of not less than 6 mm are, for instance, DeBakey artificial vessel made of woven Dacron (USCI. Co., Ltd. of U.S.A.) and Gore-Tex (Gore. Co., Ltd. U.S.A.) which is made of an expanded polytetrafuoroethylene (hereinafter referred to as "EPTFE").

Those conventional artificial vessels have pores which communicate between the inside of the vessel and the outside the vessel. When the vessel is grafted into a living body, the outside of the vessel is covered with pseudointima and the pseudointima grows into the communicating pores to cover the inside of the vessel, i.e. the vessel is organized, which prevents the formation of thrombus or occlusion by thrombus and thus makes the artificial vessel stable in the living body. The property that the communicating pores serve to make the artificial vessel organize is referred to as "porosity".

According to Sasajima et al, J. Artif. Organs 12(1), 179–182 (1983), the compliances of those artificial vessels are measured. The results are shown in Table 1.

TABLE 1

| Vessel | Compliance |
| --- | --- |
| Thoracic aorta of dog | 0.749 |
| Abdominal aorta of dog | 0.491 |
| Carotid artery of dog | 0.356 |
| Double Velour Dacron | 0.058 |
| Woven Dacron | 0.021 |
| EPTFE | 0.028 |

As shown in Table 1, the compliances of the conventional artificial vessels are much smaller than those of vital vessels, which causes various problems due to compliance mismatch such as anastomotic punnus hyperplasia long time after the grafting in a living body. Particularly, the conventional artificial vessels cannot be clinically used as an artificial vessel for artery with small diameter of not more than 6 mm because the compliance mismatch remarkably increases to make a patency of the vessel bad. Therefore self-veins are used for vascular reconstructive surgery of coronary arteries or arteries below knees.

In order to solve such compliance mismatch, a process for preparing an artificial vessel of an elastomer which has a porous wall and a compliance approximate to that of a vital vessel is disclosed in U.S. Pat. No. 4,173,689. The artificial vessel is prepared by immersing a mandrel into an elastomer solution, taking the mandrel out of the solution, coating the mandrel with the solution, and immersing into a poor solution such as water to deposit the elastomer on the mandrel. However, the process can only provide a vessel having very small pores on its wall and having a relatively dense structure. Although the compliance of the artificial vessel prepared according to the process disclosed in the U.S. Patent is surely larger than that of the conventional artificial vessel, the compliance is still smaller than that of a vital vessel and is not sufficient. In addition, since it is difficult to coat the mandrel uniformly with the elastomer solution, an artificial vessel having the same properties at all parts cannot be readily prepared.

As mentioned above, in general the smaller the diameter of an artificial vessel for an artery becomes, the more it is important that the compliance of the vessel approximates to that of a vital vessel. Although various efforts have been made to obtain an artificial vessel with a compliance approximate to that of a vital vessel, any artificial vessel having the required compliance has not been realized.

Moreover the preparations of the conventional artificial vessels are complicated, which makes the artificial vessels expensive.

Other than the compliance match, an artificial vessel requires properties such as a property that the suture cannot be readily frayed, a property that the artificial vascular material can be optionally cut to an available length, and a property that any kinking cannot be formed. In case of the woven Dacron or the woven polytetrafluoroethylene, a particular textile technique is required in order not to fray at cut ends, and a particular technique such as fellow processing is also required to avoid the formation of kinking, which makes the preparation complicate and the prices expensive. In case of the EPTFE a complicated preparation is required for extention of the PTFE, which makes also the price expensive.

As a result of the inventor's continuous studies, it has been found that an inexpensive artificial vessel having a porosity and a compliance approximate to that of a vital vessel can be prepared by extruding an elastomer solution having a cloud point from an annular nozzle at a temperature of more than the cloud point, immersing the tubular extrudate in a coagulating liquid to precipitate the elastomer, and at the same time cooling the elastomer solution with the coagulating liquid from the temperature of more than the cloud point to a temperature of not more than the cloud point. At that time the phase of the solution changes. The artificial vessel obtained has a network structure in which there are communicating pores over the entire thickness from the inner surface to the outer surface.

SUMMARY OF THE INVENTION

According to the present invention, there is provided an artificial vessel made of an elastomer having a network structure over the entire thickness of the vessel wall with small pores which communicate between the inner surface and the outer surface and having a porosity of 75 to 87.5% by volume and a compliance of 0.1 to 0.8.

DETAILED DESCRIPTION

Figure 1:
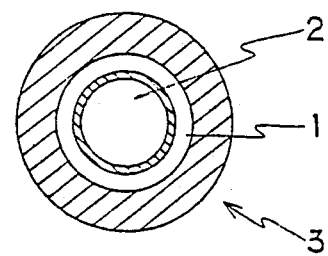
FIG. 1 shows a front view of the exit of the annular nozzle for the elastomer solution used in the present invention.

The elastomer used in the present invention is a thermoplastic elastomer which has fine blood compatibility. Namely the elastomer does not release any low molecular compound which causes acute poisoning, inflammation, hemolysis, fever and the like, and does not subject the blood to serious damage. The thermoplastic elastomer also has a superior antithrombogenicity. Examples of the elastomers are, for instance, polystyrene elastomers, polyurethane elastomers, polyolefin elastomers, polyester elastomers, elastomers which are blended with polymers except the elastomers to the extent of keeping the property of an elastomer, and a mixture thereof. From viewpoints of strength, durability and antithrombogenicity, the polyurethane elastomers are more preferable. Examples of the polyurethane elastomers are, for instance, polyurethane, polyurethaneurea and a mixture of those polymers with silicone polymers. From a viewpoint of durability in a living body, a polyether type is more preferable than a polyester type of the above-mentioned polyurethane and polyurethaneurea. A segmented polyurethane, a segmented polyurethaneurea, a segmented polyurethane or a segmented polyurethaneurea which contains fluorine atom in a hard segment or a soft segment, and a polyurethane or a polyurethaneurea disclosed in Japanese Unexamined Patent Publication (KOKAI) No. 211358/1982, which contains dimethylsiloxane in its main chain are still more preferable. Particularly preferable elastomers are the polyurethane and the polyurethaneurea which contain dimethylsiloxane in a form of the formula:

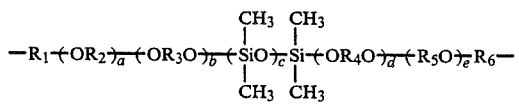

wherein $R_1$, $R_2$, $R_3$, $R_4$, $R_5$ and $R_6$ are an alkylene group having at least 1 cabon atom, preferably an alkylene group having 2 to 6 cabon atoms such as ethylene, propyrene, butylene or hexamethylene; a and e are 0 or an integer of 1 to 30; b and d are 0 or 1; c is an integer of not less than 2, and contain a polyether portion of the formula:

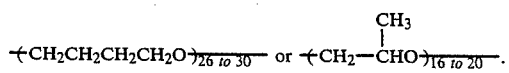

The wall of the artificial vessel of the present invention has a network structure comprising small pores over the entire thickness of the vessel wall from the inner surface to the outer surface. It is preferable that the artificial vessel substantially has no skin layer in the inner surface area and the outer surface area and the sizes of those small pores are nearly uniform. There are openings formed by the pores of the network structure in the inner and outer surfaces. Although the shape of the small pores are not particularly limited, it is preferable that the opening in the inner surface is a circle, oval and deformed shape thereof. The maximum diameter of the opening is 1 to 100 μm, more preferably 5 to 50 μm, most preferably 11 to 30 μm. When the maximum diameter is larger than 100 μm, the current of blood is disturbed and the antithrombogenicity is reduced. When the maximum diameter is smaller than 1 μm, it takes a long time to organize the artificial vessel.

The network structure in the artificial vessel of the present invention is explained herein below.

The maximum diameter of the small pore is preferably 1 to 100 μm, more preferably 3 to 75 μm, most preferably 5 to 50 μm. When the maximum diameter is larger than 100 μm, the strength of the vessel tends to be weak and its tends to be too big. When the maximum diameter is larger than 100 μm, the porosity of the vessel tends to be too big. When the maximum diameter is smaller than 1 μm, the porosity of the vessel tends to be small and the vessel tends to be too strong. Further, partition walls which form the small pores in the network structure themselves preferably have very small pores and/or holes with the maximum diameter of less than 1 μm for improving compliance and patency of the vessel. These very small pores and/or holes can be formed by replacement between a coagulating liquid and a good solvent for the elastomer which dissolves the elastomer when the elastomer solution is immersed into the coagulating liquid to precipitate the elastomer.

As mentioned above, since the artificial vessel of the present invention has the small pores which communicates the inner surface with the outer surface of the vessel wall, the organization of the artificial vessel can be achieved quickly and stably when it is grafted in a living body.

The artificial vessel of the present invention has a large compliance because the vessel is made of the elastomer and the density of the elastomer in the vessel wall is small. In addition, the compliance of the artificial vessel can be approximated to that of a vital vessel by adjusting the density of the elastomer in the vessel wall, the porosity, the strength and the thickness of the vessel wall.

Preferable compliance for an artificial vessel cannot absolutely defined because the compliance is different depending on the diameter of the vessel, the portion to be grafted, and the like. In general, since a compliance of a vital vessel which is used for vascular reconstruction surgery is about 0.1 to 0.8, the compliance is preferably within the range as mentioned above. According to the present invention the artificial vessel within any compliance within the range of 0.1 to 0.8 can be produced. The artificial vessel with a compliance of 0.1 to 0.8 can be preferably used for artery. Particularly the artificial vessel having an inside diameter of 1 to 6 mm with a compliance of 0.1 to 0.5 can be preferably used for artery with small diameter.

The "compliance approximate to that of a vital vessel" is referred to herein in the sense that the artificial vessel has the compliance approximate to that of a vital vessel having the inner diameter and the thickness of the vessel wall both approximate to those of the artificial vessel. Therefore, the artificial vessel having the inner diameter of from 2 to 6 mm, the thickness of the vessel wall of from 0.2 to 1.5 mm and the compliance of from 0.2 to 0.5 can preferably be used for arteries with small diameter and the artificial vessel having the inner diameter of from 2 to 6 mm, the thickness of the vessel wall of from 0.4 to 1.3 mm and the compliance of from 0.3 to 0.5 can more preferably be used for arteries with small diameter.

The "compliance" as used herein is defined by the equation (I):

$$C = \frac{\Delta V}{V_0 \cdot \Delta P} \times 100 \qquad (I)$$

wherein C is compliance, Vo is volume of a measured vessel at the inner pressure of 50 mmHg, ΔP is pressure difference (100 mmHg) from the inner pressure of 50 mmHg to 150 mmHg, ΔV is increasing volume of the vessel when the inner pressure rises from 50 mmHg to 150 mmHg. In practical measurement, a vessel is inserted into a closed circuit, and a volume of an injected liquid and a pressure variation in the circuit is measured by means of a microanalysis pump and a pressure gauge. From the results, the compliance can be calculated according to the equation (I).

The optimum density of the elastomer of the vessel wall varies depending on the porosity, the strength of the elastomer, the thickness of the vessel wall, the portion of a living body to be grafted. Thus, the density cannot be absolutely defined, but is preferably 0.05 to 0.35 g/cm$^3$, more preferably 0.1 to 0.3 g/cm$^3$, most preferably 0.125 to 0.25 g/cm$^3$.

This value of 0.125 to 0.25 g/cm$^3$ of the density leads to a porosity of about 75 to 87.5% by volume calculating from a specific gravity of about 1 of the usual elastomer. The range of from about 75 to 87.5% by volume of the porosity is preferable for improving the compliance and the patency.

The strength of the elastomer of the vessel wall varies depending on the effect of the density of the vessel wall and the like. Thus the strength cannot be absolutely defined, but in general the tensile strength is preferably 100 to 700 kg/cm$^2$ and the elongation at break is preferably 100 to 1500%. The thickness of the vessel wall may be agreed with that of the vital vessel to be grafted.

The compliance of the artificial vessel of this invention can be approximated to that of a vital vessel by adjusting the above-mentioned factors.

The inner surface area of the artificial vessel, that is, a surface area contacting with blood, is constructed by the skin layer of the elastomer having a superior blood compatibility. In order to improve antithrombogenicity of the vessel in the first stage of grafting in a living body, the inside wall may be coated with albumin, gelatin, chondroitin sulfuric acid, a heparinized material and the like. Also the outside wall of the artificial vessel may be reinforced with a net, a non-woven fabric and the like, in order to give a resistance against extraordinary increase of blood pressure during surgery or to maintain its durability for a long time.

The artificial vessel of the present invention with the above-mentioned structure has a porosity, a compliance approximate to that of a vital vessel and a good blood compatibility. Furthermore, since the artificial vessel of the present invention is substantially constructed by a sequence of the elastomer, the cut end of the vessel is not frayed even if the vessel is cut to any length. Also since the vessel wall is constructed by the network structure cf the elastomer, and thus has a low density, a surgical needle can easily penetrate to the vessel wall, and thus the artificial vessel can be easily sutured with vital vessels. Moreover even if the sutures are pulled, the sutures are not broken nor surgical string is deviated. Furthermore the holes formed by the needle are closed in themselves, when the needle is removed, to avoid leak of blood, because the vessel wall is made of the elastomer. In addition, the artificial vessel of this invention does not form kinking in the state that a blood pressure is exerted on the vessel wall. It is considered that the surprising property can be obtained from the fact that the compliance of the artificial vessel of the present invention is approximated to that of a vital vessel.

The preparation of the artificial vessel of the present invention is explained hereinbelow.

The artificial vessel of the invention can be prepared in accordance with a process in which an elastomer solution is extruded from an annular nozzle together with an inside coagulating liquid, and the tubular extrudate is, immediately or after passing through a dry space, immersed into an outside coagulating liquid, wherein the elastomer solution has a cloud point which is given by adding a poor solvent of the elastomer to the elastomer solution, the elastomer solution obtained is extruded at a temperature of more than the cloud point, and at least one of the inside coagulating liquid, the outside coagulating liquid and the gas contacting with the extrudate in the dry space is maintained at a temperature of not more than the cloud point of the elastomer solution.

The above-mentioned annular nozzle can extrude the elastomer solution tubularly and can be charged with the inside coagulating liquid inside thereof. An embodiment of the annular nozzle is explained in FIG. 1.

In FIG. 1 the annular nozzle 3 has an exit 1 for the elastomer solution. The inner diameter and the outer diameter of the exit 1 may be selected according to those of the desired artificial vessel. The inside coagulating liquid is extruded from an exit 2.

The elastomer solution in the present invention contains the above-mentioned elastomer, a good solvent which can dissolve the elastomer well, and a poor solvent which cannot dissolve the elastomer but is miscible with the good solvent. The elastomer solution may contain a pore-forming agent.

Examples of the good solvents are, for instance, N,N-dimethylacetamide, N,N-dimethylformamide, N-methyl-2-pyrrolidone, dioxane, tetrahydrofuran, a mixture thereof and the like. However, the good solvent should be selected according to the kind of the elastomer used.

The kind of the poor solvent varies also depending on the kind of the elastomer. Examples of the poor solvents are, for instance, water, a lower alcohol, ethylene glycol, propylene glycol, 1,4-butane diol, glycerine, a mixture thereof, and the like. The amount of the poor solvent may be selected so that the resulting elastomer solution has a desired cloud point. The term "cloud point" as used herein means a temperature at which a polymer dissolved in a solvent precipitates in a form of colloid, and the like, i.e. a temperature at which the solution changes in phase. The cloud point can be determined by observing the change of viscosity or the change of the color.

The above-mentioned pore-forming agent is used in order to give the porosity. The pore-forming agent is not particularly restricted so far as it is insoluble in the good solvent for the elastomer and can be removed during or after the preparation of the artificial vessel. Since the artificial vessel is grafted in a living body, it is desired that the pore-forming agent is pharmacologically acceptable. Examples of the pore-forming agents are, for instance, an inorganic salt such as a common salt, a water soluble saccharose such as glucose or starch, a protein and the like. The inorganic salt and the water-soluble saccharose should be treated carefully because the finely divided salt and saccharose may form the second agglomeration by moisture in the air due to their hygroscopy. From such a point of view, the protein is preferable, because even when the protein is finely divided, the fine particles do not form the second agglomeration by moisture in the air, and thus can stably produce the pores.

In addition since the protein can be easily dissolved in an alkali solution, an acid solution and a solution of an enzyme, the removal of the protein can be easily carried out. Examples of the proteins are, for instance, casein, collagen, gelatin, albumin, and the like. The particle size of the pore-forming agent is selected mainly depending on the maximum diameter of the pores formed in the inner surface area of the artificial vessel.

The amount of the pore-forming agent (percentage of weight of the pore-forming agent to weight of the elastomer in the elastomer solution) varies depending on the required porosity and the particle size of the pore-forming agent and the composition of the elastomer solution. The preferable amount is 1 to 250%, more preferably 20 to 200%, most preferably 50 to 150%. When the amount of the pore-forming agent is more than 250%, the compliance is too large, the durability against blood pressure becomes lowered, and the preparation procedures become difficult because of high viscosity of the elastomer solution. On the other hand, when the amount is less than 1%, the number of pores tends to be small, and then the required porosity may not be obtained.

The concentration of the elastomer in the elastomer solution is preferably 5 to 35% (% by weight, hereinafter the same), more preferably 10 to 30%, most preferably 12.5 to 25%. When the concentration is less than 5%, the compliance tends to be too large and the precipitated elastomer in the coagulating liquid tends not to form a tube. On the other hand, when the concentration is more than 35%, the vessel tends to be too strong relative to that of a vital vessel and the elastomer solution tends to be hardly extruded tubularly from the annular nozzle because of high viscosity of the solution.

As the coagulating liquid, a poor solvent for the elastomer which does not dissolve the elastomer but can be miscible with the good solvent for the elastomer can be employed. Examples of the coagulating liquid are, for instance, water, a lower alcohol, ethylene glycol, propylene glycol, 1,4-butane diol, glycerin, a mixture thereof and the like. A preferable coagulating liquid is water or an aqueous mixed solvent. A water-soluble inorganic salt and a good solvent for the elastomer may be added in order to modify the structures of the inside region, the inner surface area and the outer surface area of the artificial vessel wall by controlling the coagulating rate of the elastomer, or to make the procedures easy. The inside coagulating liquid and the outside coagulating liquid may be the same or different.

The preferred embodiment of the process of the present invention is explained hereinbelow.

The elastomer solution having a cloud point is fed into the annular nozzle at a constant rate, and then is extruded from the nozzle. At the same time, the inside coagulating liquid is fed into the tubular extrudate from the annular nozzle. The tubular extrudate of the elastomer solution is immersed into the outside coagulating liquid immediately or after passing through a dry space at a given dry distance. The dry distance is preferably not more than 50 cm. From a viewpoint of procedure, the extrudate is immediately immersed into the outside coagulating liquid. It is essential that the extrusion step is carried out by maintaining the elastomer solution at a temperature of more than the cloud point, and that at least one of the inside coagulating liquid, the outside coagulating liquid and the gas in the dry space is maintained at a temperature of not more than the cloud point of the elastomer solution.

According to the above procedures, the temperature of the extruded elastomer solution changes to a temperature of not more than the cloud point of the elastomer solution, which causes phase change in the solution. The solvent in the tubular elastomer solution is dissolved into the coagulating liquid as the phase of the solution changes, and then the elastomer is precipitated tubularly. The solvent is sufficiently removed from the tubularly precipitated elastomer, if desired, which cut to a proper length, to give the artificial vessel of the present invention. When the pore-forming agent is used, the pore-forming agent is removed in the manner as mentioned above.

The artificial vessel prepared by the above-mentioned process has the network structure having small pores of a uniform size over the entire thickness from the inner surface to the outer surface of the vessel wall.

Figure 2:
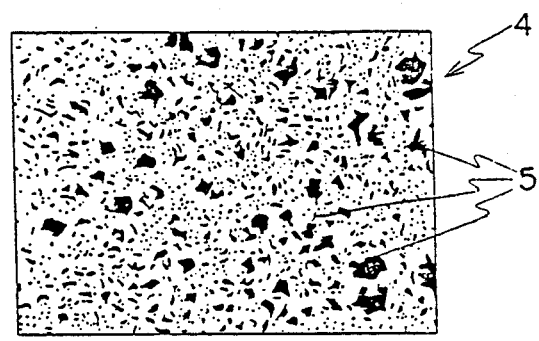
FIGS. 2 and 3 show sketched views of photographs of the inner surface and the outer surface of the artificial vessel prepared in Example 1 with a scanning type electron microscope, respectively.
Figure 3:
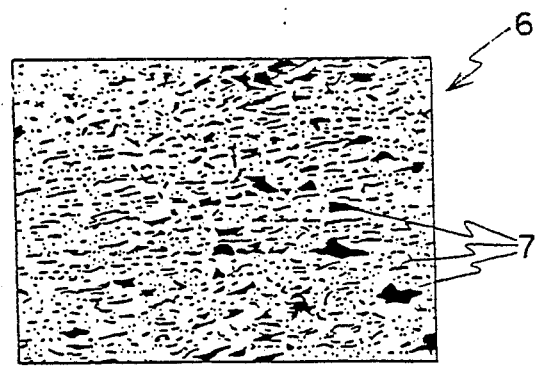

FIGS. 2 and 3 show the inner surface and the outer surface of the artificial vessel prepared in Example 1 explained hereinafter, respectively.

As shown in FIG. 2, the inner surface 4 of the artificial vessel has a number of circular or oval openings 5 of the communicating pores, and also has a number of holes. The appearance of the inner surface is similar to a surface of a pumice. On the other hand, as shown in FIG. 3 the outer surface 6 has a number of openings 7 and holes having various and indeterminate shapes. The appearance of the outer surface is similar to a surface of a relatively dense pumice.

According to the process of the present invention, the artificial vessel of a uniform quality can be readily prepared. Furthermore, any artificial vessel having a desired size can be prepared by varying the size of the annular nozzle. As a result, a price of the artificial vessel becomes lowered. In addition, any artificial vessel having a desired porosity can be prepared by varying the cloud point of the elastomer solution, the nature of the poor solvent, the amount and the particle size of the pore-forming agent, and the like. The pores thus formed can serve to support the formation of pseudointima and to make the pseudointima stable.

The artificial vessel of the present invention has a compliance of a vital vessel when the inner diameter of the artificial vessel and the thickness of the vessel wall are matched with those of the vital vessel, since the artificial vessel is made of the elastomer and has the network structure having uniform small pores in the vessel wall which is relatively bulky. The density of the elastomer in the vessel wall is usually in proportion to the concentration of the elastomer in the elastomer solution. Accordingly, when the concentration of the elastomer is 5 to 35% the density of the elastomer in the vessel wall is about 0.05 to 0.35 g/cm$^3$. Such artificial vessel is very soft because of the bulky vessel wall. Therefore, according to the process of the present invention the artificial vessel having a compliance of a vital vessel can be prepared by controlling the strength of the elastomer, the concentration of the elastomer in the elastomer solution, the cloud point of the solution, the amount and the particle size of the pore-forming agent, and the like.

The artificial vessel and the process of the present invention have the following characteristics.

(1) Compliance of the artificial vessel is approximate to that of a vital vessel.
(2) The artificial vessel has a porosity.
(3) The artificial vessel has the following essential properties for a grafting vessel.

The surface contacting with blood has a superior blood compatibility.

Surgical needle easily penetrates the vessel, and thus the vessel is easily sutured.

There is no fray at the cut ends when cut to a desired length.

Surgical string cannot be deviated at the suture.

Throughout bore formed by a needle can close in itself.

Kinking cannot be formed in the practical use that blood pressure is exerted.

(4) The artificial vessel which has the above properties of (1), (2), (3) can be prepared from the elastomer solution easily, homogeneously and inexpensively.
(5) Size of the artificial vessel can be easily adjusted by changing the size of the annular nozzle.
(6) The artificial vessel having desired pores in size and in density can be prepared by controlling the temperature change which cause the phase change or by controlling the amount and the particle size of the pore-forming agent.

Therefore, the artificial vessel of the invention can be used as an artificial vessel, an artificial vessel for by-pass, a material for patch in vascular reconstruction surgery of vital vessel, moreover, a blood access. In addition, the artificial vessel with a compliance of 0.1 to 0.8 can be used as an artificial vessel for artery. Since the artificial vessel of the present invention has the compliance approximate to that of a vital vessel, the good blood compatibility and a desired diameter, the artificial vessel can be used as an artificial vessel for artery with small diameter of 1 to 6 mm whose compliance is 0.1 to 0.5, which artificial vessel has not hitherto been available in clinical use. Such artificial vessel is preferably used for the artificial vessel in vascular reconstruction surgery of arteries below knees and for the artificial vessel of a by-pass between aorta and coronary. In addition the artificial vessel of the present invention can be used as an artificial vessel for vein by covering the outside of the vessel wall with a net having a small compliance and a substituent for a flexible vital vessel such as ureter.

The present invention is more particularly described and explained by means of the following Examples. It is to be understood that the present invention is not limited to the Examples and various changes and modifications may be made in the invention without departing from the spirit and scope thereof.

EXAMPLE 1

In 45 ml of N,N-dimethylacetamide was dissolved 20 g of polyurethane which is disclosed in Example 1 of Japanese Unexamined Patent Publication (KOKAI) No. 188458/1983, and then 35 ml of propylene glycol was added thereto. The solution had a cloud point of about 60° C. To the solution was added 20 g of casein having a particle size of 30 to 50 $\mu$m, and then dispersed with a homogenizer. After defoaming the solution sufficiently under reduced pressure, the solution was extruded at 80° C. from the annular nozzle having an inner diameter of 3 mm and an outer diameter of 4.5 mm, with a gear pump at a constant rate of about 30 cm/min. At the same time, a defoamed water of 18° C. was injected into the inside of the tubular extrudate from the inside of the annular nozzle. The extruded tubular solution was immediately immersed into water of 18° C. to precipitate the elastomer tubularly. After removing the solvent by washing with water, the elastomer was cut to a desired length. After the tubular elastomer was treated with a sodium hydroxide solution of pH about 13 to dissolve and remove the casein, an artificial vessel was obtained.

The inner and the outer diameters of the artificial vessel obtained were about 3 mm and about 4.5 mm, respectively. There are circular openings of 1 to 50 $\mu$m in diameter on the inner surface and openings having various shapes on the outer surface. Partition walls which form the communicating pores in the network structure had very small pores and holes with the maximum diameter of less than 1 $\mu$m which are formed by replacement between the good solvent and the coagulating liquid, and thus had a bulky structure.

The section of the artificial vessel wall was observed with a scanning type electron microscope. The sketched views of the inner surface and the outer surface are shown in FIGS. 2 and 3, respectively.

The porosity of the obtained vessel was 85% by volume.

The cut end of the artificial vessel was not frayed. Furthermore the suture procedure of the artificial vessel with a vital vessel was very easy, and the sutures were not frayed even if the sutures are pulled, and also the bores of a surgical needle were closed in themselves when the needle was removed.

After being cut to 8 cm, the artificial vessel was inserted into a closed circuit. The ACD blood of bovine was fed into the closed circuit by a quantitative pump which feed 0.05 ml per stroke, and the change of the inner pressure was measured. The compliance calculated according to the equation (I) on the basis of the numbers of strokes and the change of the inner pressure was 0.4.

EXAMPLE 2

A prepolymer was prepared from 2 moles of 4,4-diphenylmethane diisocyanate and 1 mole of polytetramethylene glycol having a molecular weight of 2000. The chain of the prepolymer was extended by using 1 mole of ethylenediamine to give a segmented polyurethaneurea. In a mixed solvent of 47.5 ml of N,N-dimethylacetamide and 35 ml of propylene glycol was dissolved 17.5 g of the segmented polyurethaneurea. The resulting solution had a cloud point of about 50° C. The solution was injected into the annular nozzle having an inner diameter of 3 mm and an outer diameter of 4.5 mm with a gear pump at a rate of about 40 cm/min, and then was extruded tubularly while keeping the temperature of the solution at 70° C. At the same time, a defoamed water of 20° C. was injected into the inside of the tubularly extrudate. The extruded solution was immediately immersed into water of 20° C. to precipitate the elastomer tubularly. After removing the solvent by washing with water sufficiently, the elastomer was cut to a desired length to give an artificial vessel.

The inner and the outer diameters of the artificial vessel were about 3 mm and about 4.5 mm, respectively. The cut end of the artificial vessel was not frayed and the suture procedure of the artificial vessel with a vital vessel was very easy. The vessel wall had the network structure, and there were oval or indeterminate openings on the inner surface and indeterminate openings on the outer surface. Partition walls which form the communicating pores in the network structure had very small pores and holes with the maximum diameter of less than 1 μm, which are formed by replacement between the good solvent and the coagulating liquid, and thus had a bulky structure. The compliance determined in the same manner as in Example 1 was 0.35. The porosity of the obtained vessel was 85% by volume.

As a result of the above data, it is clear that the artificial vessel has excellent properties as an artificial vessel for artery with small diameter.

What I claim is:

1. An artificial vessel comprising a vessel wall which consists essentially of a porous elastomer having a porosity of 75-87.5% by volume; said vessel wall being characterized over its entire thickness by a network structure formed by small pores having a maximum diameter of 1 to 100 μm which communicate with each other, said vessel wall being further characterized in that the partition walls which surround and form the communicating pores further contain small pores of a maximum diameter of less than 1 μm, said partition walls having a bulky structure as a result of a very small size of said very small pores, wherein the inner surface of said vessel wall has openings of a diameter of 1 to 100 μm formed by the communicating pores, and the outer surface of said vessel wall is in fluid flow communication with the inner surface of said vessel wall through the communicating pores, said vessel having a compliance of 0.1 to 0.8.

2. The artificial vessel of claim 1, wherein the inner diameter is 2 to 6 mm, the thickness of the vessel wall is 0.2 to 1.5 mm and the compliance is 0.2 to 0.5.

3. The artificial vessel of claim 1, wherein the inner diameter is 2 6 mm, the thickness of the vessel wall is 0.4 to 1.3 mm and the compliance is 0.3 to 0.5.

* * * * *